United States Patent
Gilson et al.

(10) Patent No.: US 8,849,408 B1
(45) Date of Patent: Sep. 30, 2014

(54) METHODS FOR ELECTRONIC DIRECTIONALITY OF DEEP-BRAIN STIMULATION

(71) Applicants: Richard Gilson, Oviedo, FL (US); Gregory F. Welch, Longwood, FL (US); Nizam Razack, Orlando, FL (US)

(72) Inventors: Richard Gilson, Oviedo, FL (US); Gregory F. Welch, Longwood, FL (US); Nizam Razack, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 13/734,555

(22) Filed: Jan. 4, 2013

(51) Int. Cl.
*A61N 1/00* (2006.01)
*A61N 1/36* (2006.01)

(52) U.S. Cl.
CPC .................................. *A61N 1/3606* (2013.01)
USPC ........................................................... 607/45

(58) Field of Classification Search
USPC ........................................................... 607/45
See application file for complete search history.

(56) References Cited

U.S. PATENT DOCUMENTS

| | | | |
|---|---|---|---|
| 3,628,538 A | 12/1971 | Vincent | |
| 5,474,574 A | 12/1995 | Payne | |
| 5,479,934 A | 1/1996 | Imran | |
| 5,707,396 A | 1/1998 | Benabid | |
| 5,716,377 A | 2/1998 | Rise | |
| 6,038,480 A | 3/2000 | Hrdlicka | |
| 6,301,492 B1 | 10/2001 | Zonenshayn | |
| 6,366,813 B1 | 4/2002 | DiLorenzo | |
| 6,539,263 B1 | 3/2003 | Schiff | |
| 6,597,954 B1 | 7/2003 | Fischell | |
| 6,618,623 B1 | 9/2003 | Pless | |
| 6,920,359 B2 | 7/2005 | Meadows | |
| 7,295,880 B2 | 11/2007 | Gielen | |
| 8,024,049 B1 | 9/2011 | Gilson | |
| 8,032,231 B1 | 10/2011 | Gilson | |
| 2002/0013612 A1 | 1/2002 | Whitehurst | |
| 2002/0183817 A1 | 12/2002 | Van Venrooij | |
| 2002/0188330 A1 | 12/2002 | Gielen | |
| 2003/0023297 A1 | 1/2003 | Byers | |
| 2003/0085684 A1 | 5/2003 | Tsukamoto | |
| 2003/0149457 A1 | 8/2003 | Tcheng | |
| 2003/0181954 A1 | 9/2003 | Rezai | |
| 2004/0172090 A1 | 9/2004 | Janzig | |
| 2004/0176814 A1 | 9/2004 | Singhal | |
| 2005/0055064 A1 | 3/2005 | Meadows | |
| 2005/0143790 A1 | 6/2005 | Kipke | |
| 2005/0159799 A1 | 7/2005 | Daglow | |
| 2005/0165458 A1 | 7/2005 | Boveja | |
| 2005/0171587 A1 | 8/2005 | Daglow | |
| 2010/0280572 A1 | 11/2010 | Meadows | |
| 2013/0131760 A1* | 5/2013 | Rao et al. | 607/62 |
| 2013/0138176 A1* | 5/2013 | Goetz | 607/45 |
| 2013/0245738 A1* | 9/2013 | Howard et al. | 607/116 |

OTHER PUBLICATIONS

Montgomery, E., Deep Brain Stimulation Programming, University of Wisconsin—Madison, 2006, 37 pages.

* cited by examiner

*Primary Examiner* — Robert N Wieland
(74) *Attorney, Agent, or Firm* — Timothy H. Van Dyke; Beusse, Wolter, Sanks & Maire, P.A.

(57) ABSTRACT

Methods, systems and devices to provide correction parameters for implanted electrodes by applying a cathode pulse to a bilateral implanted electrode while providing a synchronized anode on the opposite electrode. The electrical field can be "shaped" over space and time to reach more of the targeted area by selecting various combinations of active contacts. The cathode lead directs the electrical field to the target and the placement and number of anode contacts activated determines the electric field path and rate of dissipation based on vertical and horizontal distance and timing. The correction parameter can be applied to anode and cathode contacts on a single implanted lead. Each lead can have plural anode and cathode contacts each independently controllable. Active anodes and cathodes are statically or dynamically selected to generate a shaped electric field to reach the target.

22 Claims, 6 Drawing Sheets

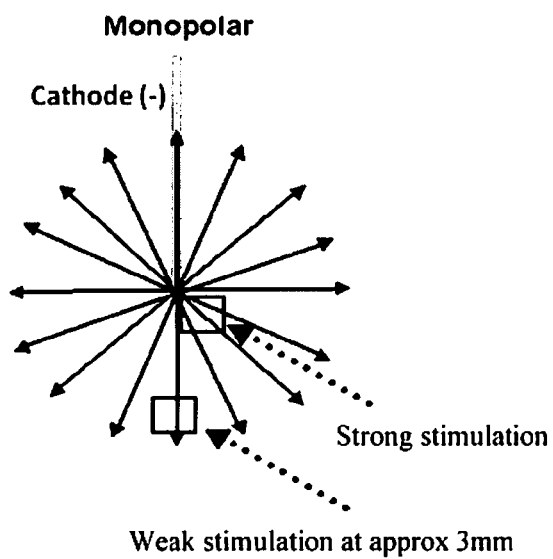
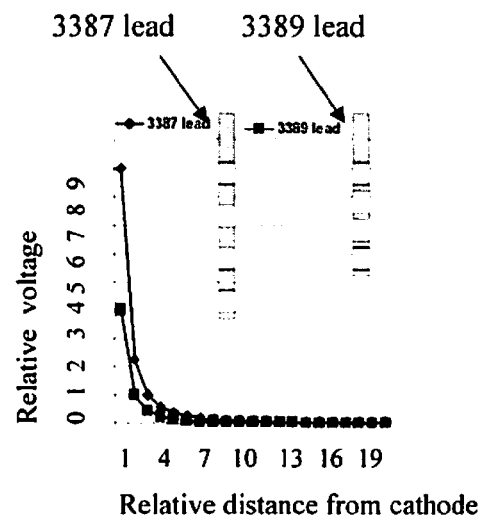
Fig. 2a PRIOR ART
Fig. 2b PRIOR ART
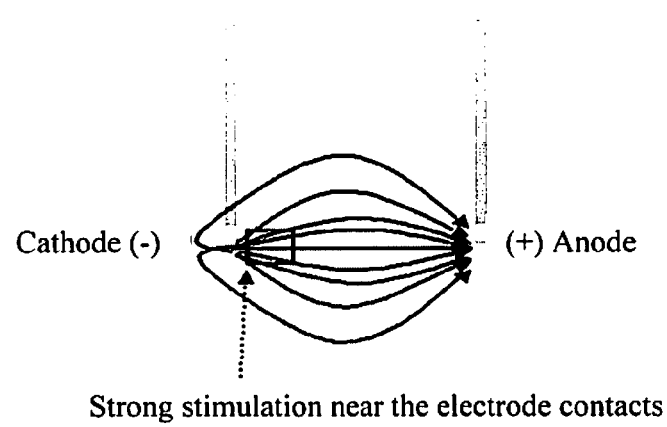
Fig. 3 PRIOR ART

METHODS FOR ELECTRONIC DIRECTIONALITY OF DEEP-BRAIN STIMULATION

FIELD OF THE INVENTION

This invention relates to medical implants and, in particular, to methods, systems and devices for electronic directionality of deep brain stimulation.

BACKGROUND AND PRIOR ART

Brain stimulation devices can be used for treatment of depression and/or a number of neurological disorders and chronic degenerative diseases.

U.S. Pat. No. 7,295,880 issued Nov. 30, 2007 to Gielen teaches methods and devices for monitoring the battery life of an implantable deep brain stimulation device including modifying the therapy to increase the battery life of the implantable pulse generator to allow the patient time to seek medical attention.

U.S. Patent Pub. No. US2005/0165458 by Boveja published on Jul. 28, 2005 teaches using electroconvulsive therapy to the brain and pulsed electrical stimulation to the vagus nerve using implantable pulse generator and electrodes on the exterior of the head. The therapy can be in any order, ay combination or any sequence. The implantable device can include wireless communication capability.

U.S. Patent Publication No. 210/0280572 by Meadows, et al., published on Nov. 4, 2010, is a continuation of U.S. Patent Pub. 2005/0055064, now abandoned, which is a continuation-in-part of U.S. Pat. No. 6,920,359 issued on Jul. 19, 2005, teaches an open loop deep brain stimulation system that uses a multichannel implantable pulse generator small enough to be implanted directly into the cranium of the patient. The system also has support for two leads, each lead having plural electrodes; and the system including a wireless link. The publication does not describe use of the system such as cathode and anode configuration, pulse duration strength such as current and voltage, or directionally of the pulse, etc.

Montgomery, et al "Deep Brain Stimulation Programming" publication, University of Wisconsin, (Feb. 20, 2006), is directed toward electroconvulsive therapy as electrical stimulation to the vargus nerve using an implantable or external pulse generator and ECT electrodes on the head. The implantable device can include wireless communication capability. Montgomery takes an in depth review of deep brain stimulation with a single lead having multiple ring contacts including the implantation of the lead, the stimulation characteristics, results, adverse effects and possible causes and remedies.

A number of neurological disorders and many neurodegenerative diseases like Parkinson's disease involve, or eventually progress to involvement of both brain hemispheres; requiring electrode implants in both sides. Bilateral implanted electrodes can be powered by two separate implantable pulse generators as (IPGs) shown in FIG. 1a or by one that serves both electrodes as shown in FIG. 1b. If there are two separate IPGs, their pulses are unsynchronized. If there is only one dual-channel IPG that serves both electrodes, the pulses are exactly synchronized, energizing contacts at the same time.

There is good evidence that bilateral stimulation has a synergetic effect on therapeutic efficacy, suggesting that target sites are close enough for the contralateral electrical fields to interact. Normally, the voltages being used clinically in the subthalamic nucleus (STN), for example, are in the range of 2 to 3 V and the electrode impedance is typically between 750 and 1500 ohms. The best estimates of current spread thus translate into distances of 2 to 3 mm radially from a monopolar contact (approximately 1-1.5 mm diameter per mA, decreasing in stimulating intensity with distance as shown in FIGS. 2a and 2b.

FIG. 2a illustrates monopolar current filed produced with monopolar stimulation. FIG. 2b is a graph showing the relative monopolar loss of voltage in regard to relative distance from the cathode with two commonly used leads, results from the 3387 lead is shown with circles while the results with the 3389 lead are shown with squares. As shown in the graph, as the distance from the cathode increases, the relative voltage decreases with both the 3387 lead and the 3389 lead.

Typically, monopolar stimulation is first tested with a single contact on the lead set as the cathode and the pulse generator and lead set as the anode. Although generally one contact is used as the cathode, it is occasionally useful to activate two adjacent contacts for a broader field of current diffusion. Bipolar stimulation is accomplished using one electrode contact as the anode and an adjacent electrode as the cathode. This configuration is advantageous if adverse effects due to current spread to adjacent structures limits efficacy of stimulation. Bilateral anode and cathode contacts elongate and diffuse the current field as shown in FIG. 3, allowing stimulation of nearby brain sites while minimizing stimulation of more distant sites in between in other directions. As described in relation to the monopolar current field shown in FIG. 2a, the strongest stimulation occurs near the electrode contacts in the bipolar stimulation as well.

A problem associated with the previously described deep brain stimulation devices is that when the contact is displaced more substantially medial-lateral or anterior-posterior to the target center, or there is an electrode shift, the only option now is for another surgery to re-implant them.

What is need is a computerized alternative that resolves the problem without the risks incurred with additional brain surgery.

SUMMARY OF THE INVENTION

A primary objective of the present invention is to provide methods, systems and devices for correcting parameters for displaced electrodes of a deep brain stimulation device by applying a cathode pulse to a single or a plurality of ipsilateral contacts, preferably directional contacts, while providing a synchronized anode on the contralateral electrode, or separately placed but similarly-acting anode contact(s) wired as a skull plate or the like, favorably positioned to draw the current field across the prime targeted area of the brain.

A secondary objective of the present invention is to provide methods, systems and devices for use with multiple, bilateral implant leads, or separate plate as anode contacts, efficaciously placed to the target to electronically "draw" the current flow in the direction of the target site.

A third objective of the present invention is to provide methods, systems and devices for deep brain stimulation devices with two or more leads or separate plates each having one or more contacts to turn the anode lead on the stimulating lead "off" at the time of stimulation when the adjacent cathode ring is turned "on" and simultaneously turning the anode ring on another lead (bilateral lead) "on" to draw the current density across the nearby target.

A fourth objective of the present invention is to provide methods, systems and devices for implantable pulse generators for deep brain stimulation that can be retrofitted to existing implants to avoid surgical re-implantation.

A fifth objective of the present invention is to provide methods, systems and devices for implantable pulse generators for deep brain stimulation that provides the advantage of additional parameters for computerized adjustment of the electric field for therapeutic efficacy; allows for correction for suboptimal electrode placement in the horizontal planar; potential to avoid surgical re-implantation; and the implantable pulse generator according to the present invention can be retro-fitted to existing electrode lead implants.

A sixth objective of the present invention is to provide methods, systems and devices for implantable pulse generators for deep brain stimulation that provides the advantage of additional parameters for computerized adjustment of the electric field for therapeutic efficacy; allows for correction for suboptimal electrode placement with minimal surgical implantation of separate anode contact(s), skull plate or the like, favorably positioned to draw the current field across the prime targeted area of the brain.

A deep brain stimulation system can include an implanted electrode lead having plural independently controllable cathode contacts and plural independently controllable anode contacts, an implantable pulse generator for controlling the bilateral implanted electrodes to independently generate an electric field from one or more electrode cathode contacts and draw a current from the generated electric field toward one or more electrode anode contacts or separate skull plates through a targeted area, and a connection to the implantable pulse generator.

Alternatively, the implanted electrode can be a separately implanted plate or separately implanted contact.

The IPG can include a processor for executing a set of instructions to activate and deactivate the implanted electrode plural cathode and anode contacts, and a power source to supply power to the implantable pulse generator.

The implanted electrode can include one single electrode lead having one or more anode contacts, and one or more cathode contacts each separated from adjacent contacts by a neutral space, each one of the anode and cathode contacts independently controllable. The cathode contacts and anode contacts can be ring contacts. The cathode contacts and anode contacts can be split ring contacts or separately implanted plate or contact.

The implanted electrode can include bilateral electrode implants consisting of one single ipsilateral electrode lead and one contralateral electrode lead, the bilateral electrode implants connected with one dual channel implantable pulse generator. The cathode contacts and anode contacts can be ring contacts. The cathode contacts and anode contacts can be split ring contacts or separately implanted plate or contact.

An IPG can include a processor for executing a set of instructions to activate and deactivate one or more contacts on an implanted electrode lead connected with the implantable deep brain stimulation pulse generator. The set of instructions can include selecting and energizing one or more cathode contacts on the connected implanted electrode lead, selecting and energizing one or more anode contacts simultaneously. The generator can include a power source to supply power to the implantable pulse generator.

The set of instructions can include selecting one or more cathode contacts on one of an ipsilateral and a contralateral implanted electrode lead or separately implanted plate or contact, and selecting one or more cathode contacts on an opposite one of the ipsilateral and the contralateral implanted electrode lead or separately implanted plate or contact.

The set of instructions can further include alternating the selection of contacts on the ipsilateral lead and the contralateral electrode or separately implanted plate or contact lead as the cathode contact, and alternating the selection of contacts on the opposite one of the ipsilateral lead and the contralateral electrode or separately implanted plate or contact lead as the anode contact. The set of instructions further can include varying a frequency of an electrical pulse from the implanted electrode lead.

The set of instructions further can include varying a voltage of an electrical pulse from the implanted electrode lead. The set of instructions further can include varying a pulse width of an electrical pulse from the implanted electrode lead.

A method for delivering a stimulation current to a targeted area of a brain with a deep brain IPG can include the steps of executing a set of instruction by a controller that is, within, or is associated with the IPG, and connected with an implantable electrode lead. The set of instructions can include selecting an electrode on an implanted electrode lead as a cathode and a different contact as an anode on the contralateral implanted lead or separately implanted plate or contact, generating a pulsed electrical field from the cathode contact, simultaneously drawing a current from the electric field toward the selected anode to stimulate the targeted area of the brain, alternating the selection of the anode and the cathode for each next pulse, and adjusting the electric field between the selected cathode contact and the selected anode contact.

The selecting step can include the steps of selecting one or more cathode contacts on one of an ipsilateral and a contralateral implanted electrode lead, and selecting one or more cathode contacts on an opposite one of the ipsilateral and the contralateral implanted electrode lead or separately implanted plate or contact.

The method can further include the steps of alternating the selection of contacts on the ipsilateral lead and the contralateral electrode lead as the cathode contact, and alternating the selection of contacts on the opposite one of the ipsilateral lead and the contralateral electrode lead or separately implanted plate or contact as the anode contact. The method can further include the step of varying a frequency of an electrical pulse from the implanted electrode lead. The method can further include the step of varying a voltage of an electrical pulse from the implanted electrode lead. The method can further include the step of varying a pulse width of an electrical pulse from the implanted electrode lead.

Further objects and advantages of this invention will be apparent from the detailed description of preferred embodiments that are described in the following and illustrated schematically in the accompanying drawings.

BRIEF DESCRIPTION OF THE FIGURES

FIG. 2a shows the radial stimulation current field from a monopolar lead

FIG. 2b is a graph showing the relative voltage in regard to relative distance from the cathode.

FIG. 3 shows the stimulation current field from a pair of bipolar leads with one lead as a cathode and the other lead as the anode.

DESCRIPTION OF THE PREFERRED EMBODIMENTS

Figures 1A, 1B:
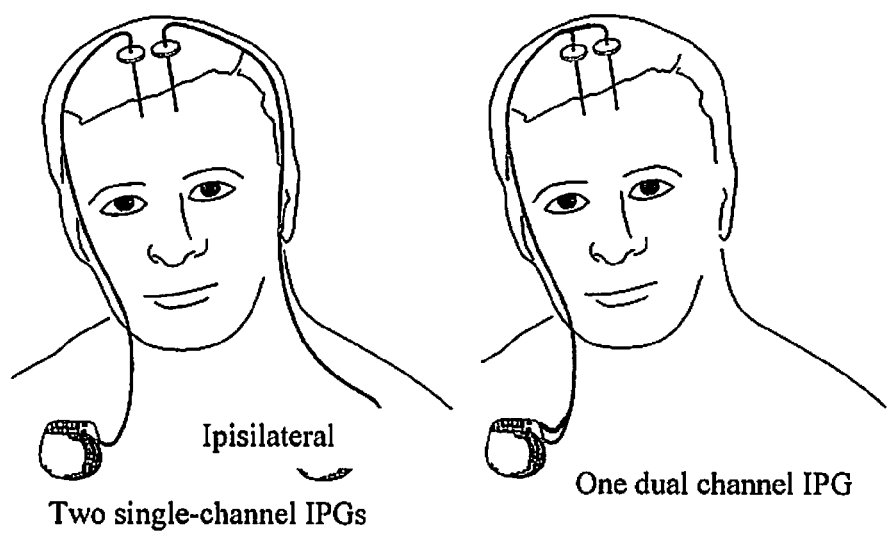
FIG. 1a shows an example of bilateral implants with a single-channel implantable pulse generator.
FIG. 1b shows an example of bilateral implants with dual channel implantable pulse generators.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

The following is a list of reference numerals used in the description and the drawings to identify components:
30 electrode lead
50 ring contacts
100 deep brain stimulation device
110 ipsilateral electrode lead
115 anode ring contacts
120 contralateral electrode lead
125 anode ring contacts
150 implantable IPG Deep-brain stimulation (DBS) has been successful in treating symptoms of a number of neurological disorders and chronic degenerative diseases, including Parkinson's disease. Post-operative clinical results and imaging confirm that precise stimulation of targeted brain areas is essential for best therapeutic efficacy and for reduced side effects. Stimulation of intended structures, while avoiding other nearby brain areas, depends on exact surgical placement of microelectrode contact(s) and careful adjustment of the stimulating electrical field. The goal is to center the contact in the intended structure and to confine the current density from the contacts to a selected area that is often only about an order of magnitude larger than one of the electrode contacts itself, which is approximately 1.5 mm×approximately 1.27 mm.

Figure 4A:
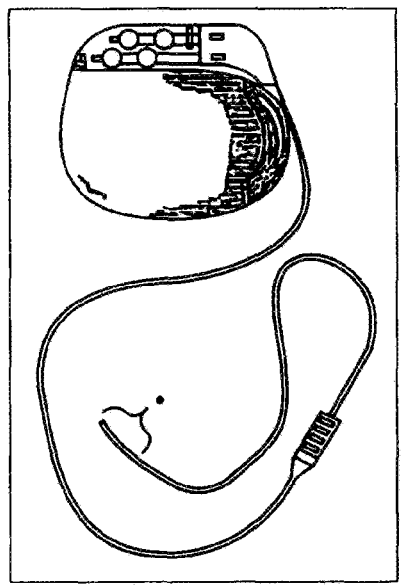
FIG. 4a shows an implantable pulse generator and electrode lead.
Figure 4B:
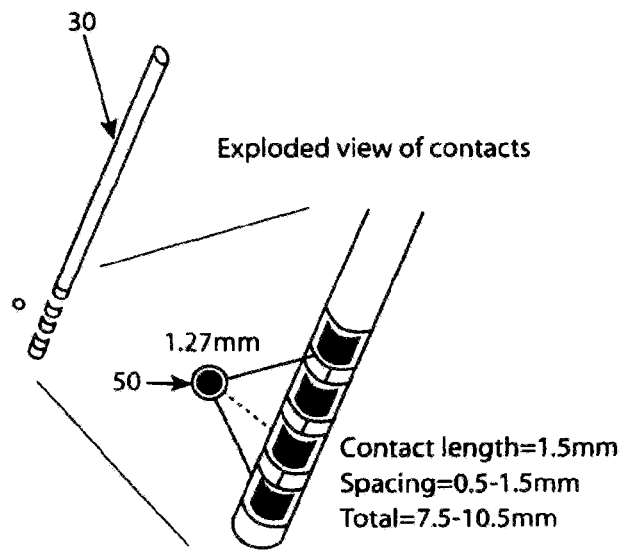
FIG. 4b is an exploded view of the electrode lead showing four ring contacts.

Variability is introduced by many factors including individual differences in anatomy, imaging interpretation, and intra-operative movement, as well as by voltage, duration and frequency of the stimulation. Existing technology by the inventor, Richard D. Gilson, as described in U.S. Pat. Nos. 8,032,231 and 8,024,049 and U.S. patent application Ser. No. 13/250,362 filed Sep. 30, 2011, each assigned to the same assignee and which are all incorporated by reference, allows for superior-inferior adjustments by selecting one or more of four contacts 50 within millimeters from each other on the implanted electrode leads 30 as shown in FIGS. 4*a* and 4*b*. FIG. 4*a* shows an implantable pulse generator and electrode lead and FIG. 4*b* is an exploded view of the electrode lead showing four ring contacts.

Figure 5:
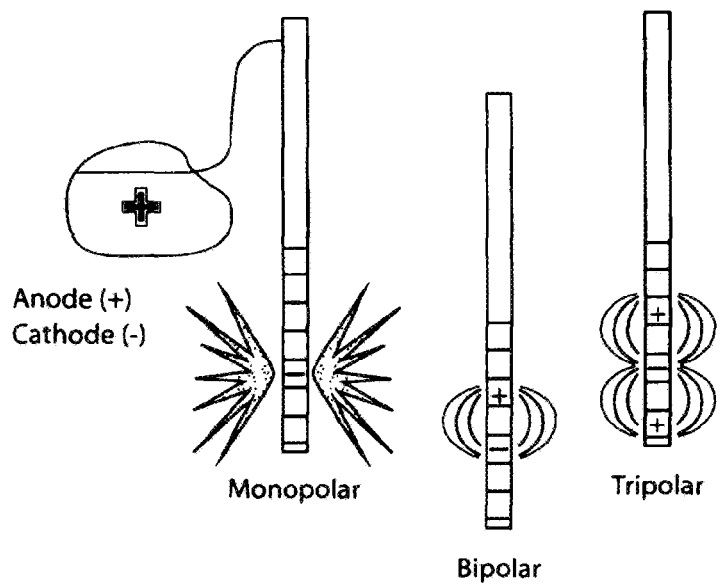
FIG. 5 shows examples of the field generated by, from left to right, a monopolar, bipolar and tripolar contact selection.

One of the problems with today's circular electrode contacts on implanted electrode leads for deep brain stimulation is that the electronic current flow is also a circular outflow from the cathode "ring" to an adjacent anode "ring" on the same lead as shown in FIG. 5. This is fine assuming that the electrode contact is centered in the target site, e.g., the STN, but is highly inefficient and potentially fraught with side effects if the contact misses the small brain target because only part of the current flow hits the target and most of it flows elsewhere in the brain which can cause unintended consequences.

Figure 6:
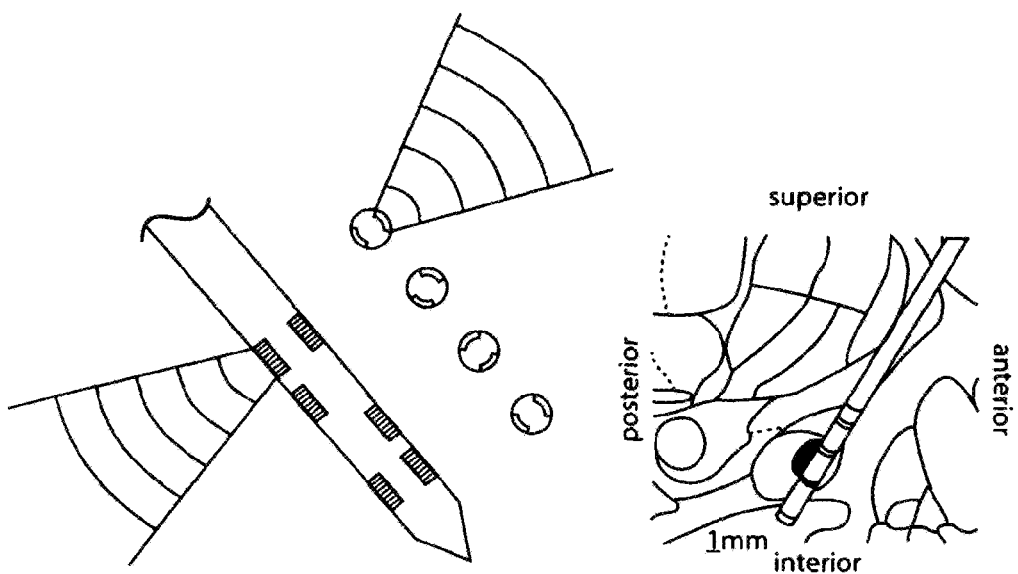
FIG. 6 shows the electric field generated by split-ring direction contacts.

The Gilson '049 patent describes a method as shown in FIG. 6 using split-ring directional contacts for directing the electrical field to create a "lighthouse effect" whereby only the split ring contact sections pointing towards the targeted neuronal area are activated. The contact section to be activated is selected on the basis of clinical efficacy.

A number of neurological disorders and many neurodegenerative diseases like Parkinson's disease involve, or eventually progress to involvement of both hemispheres, thus requiring electrode implants in both sides as shown in FIG. 1*b*. The methods, systems and devices of the present invention is advantageous for patients with multiple or bilateral implants and with contacts placed laterally to the target when the contact 50 of an implanted electrode lead 30 is displaced medial-lateral or anterior-posterior to the target center, still within the STN but not ideally placed.

One approach to the problem for misplaced electrodes has been to position plural contacts on the lead to allow selections of different contacts bested placed superior or inferior for clinical efficacy. However, anterior-postier or medialateral "misses" may require lead re-implantation to reduce symptomatology.

Figure 7:
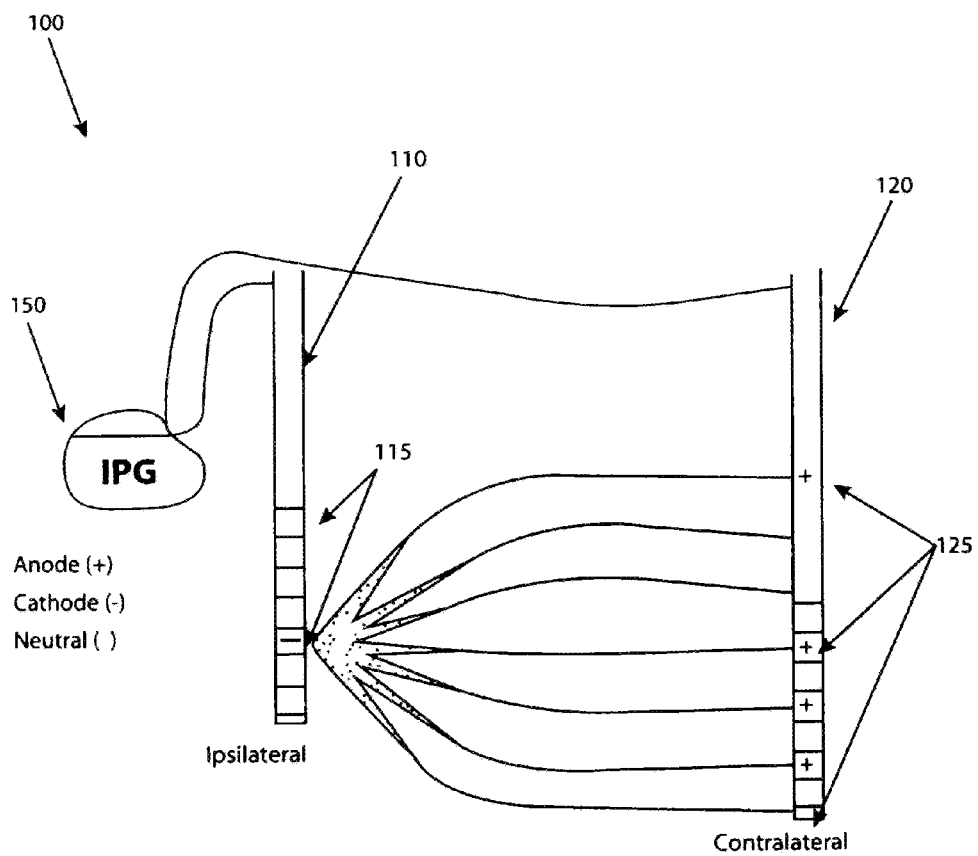
FIG. 7 shows an example of an ipsilateral and contralateral electrode lead configuration according to the present invention with a single implantable pulse generator.

The first embodiment of the present invention provides two spaced apart electrode leads connected and controlled by a single implantable pulse generator 150. FIG. 7 shows an example of an ipsilateral and contralateral electrode lead configuration 100 according to the present invention with a single implantable pulse generator. As shown, the ipsilateral lead 110 has two or more ring or directional contacts 115 that function as cathodes and the contralateral lead 120 has two or more ring or directional contacts 125 that function as anodes. Each contact is separated from adjacent contacts by a neutral space. The processor controlled implantable pulse generator 150 selects one or more of the ipsilateral contacts as cathodes and selects one or more of the contacts on the contralateral lead as anodes.

In a preferred embodiment, the present invention provides a correction parameter for displaced electrodes by applying a cathode pulse to a single or a plurality of ipsilateral contacts 115 that are preferably directional contacts as described in the '049 patent while providing a synchronized anode 125, on the contralateral electrode 120, or separately implanted plate or contact. The electrical field can be "shaped" over space and time to reach more of the targeted site, and less of other sites nearby, by selecting and using various combinations of active contacts 50 on the electrode array. The cathode lead is selected to direct the higher electrical field to the target area and the placement and number of anode contacts activated determines path the electric field takes and the rate of dissipation of the electric field based on distance vertically and horizontally, and the pulse timing.

In another embodiment, the correction parameter is applied to the anode and cathode contacts on a single implanted lead as shown in FIG. 5 which shows from left to right monopolar, bipolar, and tripolar contact section. Each one of the leads can have plural anode contacts and plural cathode contacts that are each independently controllable. The active anodes and cathodes are selected to generate a shaped electric field to reach the target site.

In a preferred embodiment, the cathode pulses alternate between the two bilateral electrode leads. In other words, one or more cathode contacts on the ipsilateral electrode lead are energized to produce the first pulse. After the first pulse, the contralateral electrode lead can be activated to produce the second pulse. The number, order, and timing of cathode pluses produced from each one of the ipsilateral and the contralateral electrode leads can be varied for the best therapeutic efficacy and for reduction of side effects. Stimulation of the intended structures, while avoiding other nearby brain areas, depends on the careful adjustment of the stimulating electrical field. As previously discussed, the system, methods and devices of the present invention allows the size and shape of the electrical filed to be varied over space and time to achieve the best clinical results.

One method involves turning the anode contact on the stimulating ipsilateral lead "off" at the time of stimulation when the cathode contact is turned "on" and approximately simultaneously turning the anode on the bilateral lead or separately implanted plate or contact "on" to draw current density across the nearby target. The method is applicable to bilateral implanted electrodes as well as a single implanted electrode. Additionally, this and the other disclosed and similar methods can be applied as a remedial measure in place of re-implanting electrode leads by retrofitting with an implantable pulse generator according to the present invention.

Figure 8:
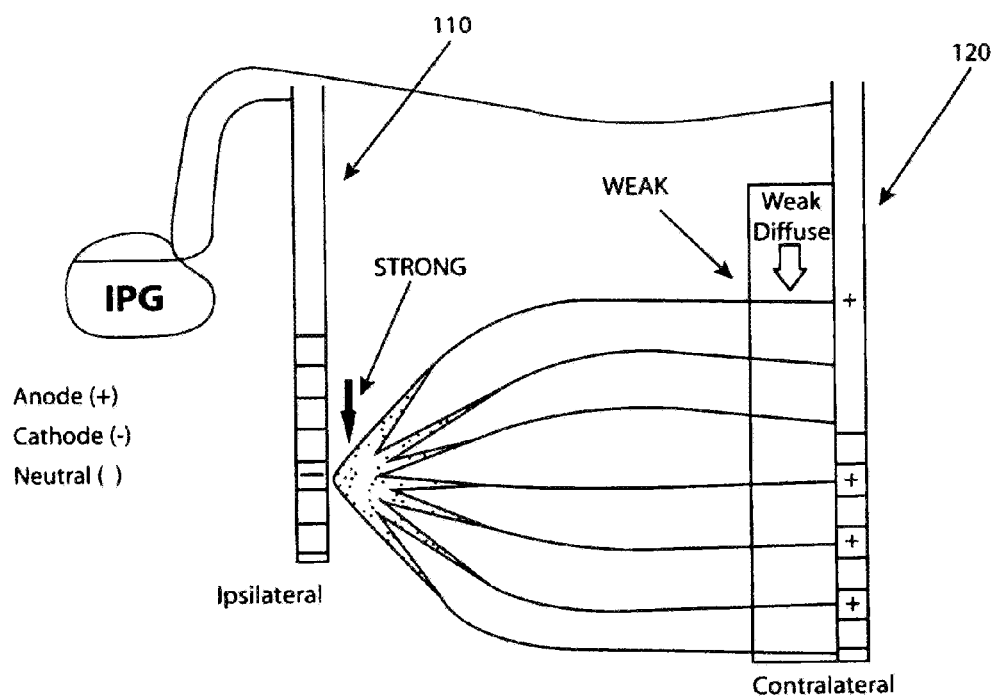
FIG. 8 shows electrical field strength and weakness of the ipsilateral and contralateral electrode lead configuration shown in FIG. 7.

FIG. 8 shows an example of the electrical field strength and weakness of the ipsilateral and contralateral electrode lead (or separately implanted plate or contact) configuration shown in FIG. 7. The effect allows the strong electrical field of the pulse to be draw medially across the ideal target site, displaced medially and then dissipated by distance and diffusion. Simply put, the strongest field is close to the cathode with the field weakening as the distance between the cathode and anode increases. Similarly, the strength of the electric field also decreases as the electric field is spread over a greater distance at the anode electrode lead as shown in the example in FIG. 8.

As shown, the shape of the electric field can be shaped by selection of active cathodes and anodes. This allows the treatment to be adjusted to targeted brain areas which is essential for best therapeutic efficacy and for reduced side effects.

One skilled in the art should realize that the particularities in the electrical field should not be construed as limitation of the preferred embodiment. Various system configurations and corresponding components may be chosen and optimized for a particular application to achieve a desired performance and other methods to determine location, size and shape of the electric field, such as selecting two or more cathodes and only one anode or two or more cathodes and two or more anodes and the like.

Alternately, two spaced apart leads with each lead capable of switching between being an anode lead and a cathode lead. For example, in the preferred embodiment, the cathode pulses would alternate between the two bilateral electrode leads. After the first pulse from the ipsilateral lead, the contralateral electrode would be activated depending on the contact position relative to the target area as described above.

In another preferred embodiment, there can be a separately implanted plate or contact that can act as a dynamically acting anode, as described above.

In yet another preferred embodiment, there can be one electrode lead as described in the '049 patent with the anode and cathode on the same electrode lead.

Other variations include the use of different combinations of contacts on the anode or cathode electrode arrays.

The following example relates to the two electrode lead configuration shown for example in FIG. 1b in conjunction with FIG. 8. The implantable pulse generator includes firmware/software for implementing the preferred embodiment. The implementation steps include isolation of the anode on the ipsilateral electrode during the cathode pulse and redirecting the anode to the contralateral electrode or separately implanted plate or contact. Computerized pulse control would successively select and activate the specific electrode contacts using fast electronic switching. This would add programming flexibility to existing stimulation parameters that are typically adjustable to have a selected frequency between approximately 0 to approximately 185 Hz, pulse width in the range of approximately 60 to approximately 450 seconds, a voltage between approximately 0 and approximately 10.5 Volts, and stimulating contacts on the same electrode as described in regard to monopolar or multi-polar stimulation.

The present invention provides the advantage of additional parameters for computerized adjustment of the electric field for therapeutic efficacy; allows for correction for suboptimal electrode placement in the horizontal planar; potential to avoid surgical re-implantation (or minimal surgical skull plate implant); and the implantable pulse generator according to the present invention can be retro-fitted to existing electrode lead implants.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A deep brain stimulation system comprising:
   an implanted electrode member having plural independently controllable cathode contacts and plural independently controllable anode contacts, the electrode member being selected from at least one of an implanted electrode lead or separately implanted plate or separately implanted contact;
   at least one implantable pulse generator for controlling the implanted electrode member to independently generate an electric field from one or more electrode cathode contacts and draw a current from the generated electric field toward one or more electrode anode contacts through a targeted area; and
   a connection between the implanted electrode member and the implantable pulse generator.

2. The system of claim 1 wherein the implantable pulse generator comprises:
   a processor for executing a set of instructions to activate and deactivate the implanted electrode plural cathode and anode contacts; and
   a power source to supply power to the implantable pulse generator.

3. The system of claim 2 wherein the implanted electrode member comprises:
   one single electrode lead having one or more anode contacts and one or more cathode contacts each separated from adjacent contacts by a neutral space, each one of the anode and cathode contacts independently controllable.

4. The system of claim 3 wherein the cathode contacts and anode contacts are ring contacts.

5. The system of claim 3 wherein the cathode contacts and anode contacts are split ring contacts.

6. The system of claim 1 wherein the implanted electrode member comprises:
   bilateral electrode implants consisting of one single ipsilateral electrode lead and one contralateral electrode lead, the bilateral electrode implants connected with one dual channel implantable pulse generator.

7. The system of claim 6 wherein the cathode contacts and anode contacts are ring contacts.

8. The system of claim 6 wherein the cathode contacts and anode contacts are split ring contacts.

9. The system of claim 6, further comprising:
a cathode set of instructions for selecting and energizing one or more cathode contacts on one of the ipsilateral and contralateral electrode lead simultaneously; and
an anode set of instructions for selecting and energizing one or more anode contacts on an opposite one of the ipsilateral and contralateral electrode lead simultaneously.

10. The system of claim 6 further comprising:
a set of alternating instructions for:
alternating selection of the one or more cathodes on the ipsilateral electrode lead and contralateral electrode lead; and
alternating selection of the one or more anodes on an opposite one of the ipsilateral and contralateral electrode leads or separately implanted plate or contact.

11. An implantable deep brain stimulation pulse generator comprising:
a processor for executing a set of instructions to activate and deactivate one or more contacts on an implanted electrode lead connected with the implantable deep brain stimulation pulse generator, the set of instructions comprising:
selecting and activating one or more cathode contacts on the connected implanted electrode lead; and
selecting and deactivating one or more anode contacts on the connected implanted electrode lead simultaneously; and
a power source to supply power to the implantable pulse generator.

12. The implantable stimulation pulse generator of claim 11 wherein the set of instructions further comprise:
selecting one or more cathode contacts on one of an ipsilateral and a contralateral implanted electrode lead or separately implanted plate or contact; and
selecting one or more cathode contacts on an opposite one of the ipsilateral and the contralateral implanted electrode lead or separately implanted plate or contact.

13. The implantable stimulation pulse generator of claim 12 wherein the set of instructions further comprise:
alternating the selection of contacts on the ipsilateral lead and the contralateral electrode lead as the cathode contact; and
alternating the selection of contacts on the opposite one of the ipsilateral lead and the contralateral electrode lead or the separately implanted plate or the contact as the anode contact.

14. The implantable stimulation pulse generator of claim 11 wherein the set of instructions further comprise:
varying a frequency of an electrical pulse from the implanted electrode lead.

15. The implantable stimulation pulse generator of claim 11 wherein the set of instructions further comprise:
varying a voltage of an electrical pulse from the implanted electrode lead.

16. The implantable stimulation pulse generator of claim 11 wherein the set of instructions further comprise:
varying a pulse width of an electrical pulse from the implanted electrode lead.

17. A method for delivering a stimulation current to a targeted area of a brain with a deep brain stimulation pulse generator comprising the steps of:
executing a set of instructions by a controller connected with an implantable electrode lead, the set of instructions comprises the steps of:
selecting an electrode on an implanted electrode lead as a cathode and a different contact as an anode;
generating a pulsed electrical field from the cathode contact;
simultaneously drawing a current from the electric field toward the selected anode to stimulate the targeted area of the brain;
alternating the selection of the anode and the cathode for each next pulse; and
adjusting the electric field between the selected cathode contact and the selected anode contact.

18. The method of claim 17 wherein the selecting step comprises the steps of:
selecting one or more cathode contacts on one of an ipsilateral and a contralateral implanted electrode lead or separately implanted plate or contact; and
selecting one or more cathode contacts on an opposite one of the ipsilateral and the contralateral implanted electrode lead or the separately implanted plate or the contact.

19. The method of claim 17 further comprising the steps of:
alternating the selection of contacts on the ipsilateral lead and the contralateral electrode lead as the cathode contact; and
alternating the selection of contacts on the opposite one of the ipsilateral lead and the contralateral electrode lead or the separately implanted plate or the contact as the anode contact.

20. The method of claim 17 further comprising the step of:
varying a frequency of an electrical pulse from the implanted electrode lead.

21. The method of claim 17 further comprising the step of:
varying a voltage of an electrical pulse from the implanted electrode lead.

22. The method of claim 17 further comprising the step of:
varying a pulse width of an electrical pulse from the implanted electrode lead.

* * * * *